United States Patent
Naghavi

(10) Patent No.: US 8,109,982 B2
(45) Date of Patent: Feb. 7, 2012

(54) NON-INVASIVE MODULATION OF THE AUTONOMIC NERVOUS SYSTEM

(76) Inventor: Morteza Naghavi, Houston, TX (US)

(*) Notice: Subject to any disclaimer, the term of this patent is extended or adjusted under 35 U.S.C. 154(b) by 1565 days.

(21) Appl. No.: 11/425,919

(22) Filed: Jun. 22, 2006

(65) Prior Publication Data

US 2006/0293719 A1 Dec. 28, 2006

Related U.S. Application Data

(60) Provisional application No. 60/693,122, filed on Jun. 23, 2005.

(51) Int. Cl.
*A61F 7/00* (2006.01)
(52) U.S. Cl. .......................... 607/96; 607/108
(58) Field of Classification Search ............. 607/40, 607/41, 96–104, 108, 114; 600/9–14, 29–32; 128/885, 899, 882; 219/549, 211
See application file for complete search history.

(56) References Cited

U.S. PATENT DOCUMENTS

| | | | | |
|---|---|---|---|---|
| 3,680,563 A * | 8/1972 | Forrest | ............... | 607/112 |
| 4,205,671 A * | 6/1980 | Lassen | ............... | 128/886 |
| 4,764,665 A * | 8/1988 | Orban et al. | ............... | 219/549 |
| 5,123,407 A * | 6/1992 | Dewhurst | ............... | 602/2 |
| 5,824,996 A * | 10/1998 | Kochman et al. | ............... | 219/529 |
| 6,066,164 A * | 5/2000 | Macher et al. | ............... | 607/96 |
| 6,074,414 A | 6/2000 | Haas et al. | | |
| 6,191,156 B1 * | 2/2001 | Kifor et al. | ............... | 514/381 |
| 6,294,758 B1 * | 9/2001 | Masao et al. | ............... | 219/217 |
| 6,353,940 B1 | 3/2002 | Lyden | | |
| 6,366,814 B1 * | 4/2002 | Boveja et al. | ............... | 607/45 |
| 6,840,955 B2 | 1/2005 | Ein | | |
| 7,089,995 B2 | 8/2006 | Koscheyev et al. | | |
| 7,415,308 B2 * | 8/2008 | Gerber et al. | ............... | 607/41 |
| 2002/0029410 A1 | 3/2002 | Szymocha et al. | | |
| 2003/0178032 A1 * | 9/2003 | Ingle et al. | ............... | 128/898 |

OTHER PUBLICATIONS

James Frith et al. "Autonomic dysfunction in chronic liver disease", Liver International (2009) 1478-3223.
William C. de Groat "Integrative control of the lower urinary tract: preclinical perspective" British Journal of Pharmacology 147, (2006) S25-S40.
Steven A. Kaplan, MD "Update on the American Urological Association Guidelines for the Treatment of Benign Prostatic Hyperplasia" Reviews in Urology 8 (Suppl 4) (2006) S10-S17.
D.L. Kellogg, Jr. et al. "Nitric oxide and cutaneous active vasodilation during heat stress in humans" J Appl Physiol 85 (1998) 824-829.
D.L. Kellogg, Jr. et al. "Role of nitric oxide in the vascular effects of local warming of the skin in humans", J Appl Physiol 86 (1999) 1185-1190.
A. R. Moritz, M.D. et al. "Studies of Thermal Injury, The Relative Importance of Time and Surface Temperature in The Causation of Cutaneous Burns", Am J. Pathol 23(5) (1947) 695-720.

(Continued)

*Primary Examiner* — Roy Gibson
(74) *Attorney, Agent, or Firm* — David McEwing

(57) ABSTRACT

The present invention is directed to methods and apparatus for modulation of the sympathetic-parasympathetic balance by application of heat, carotid and/or ocular message to reduce sympathetic tone or increase parasympathetic tone in a target muscle system to relieve a symptom of urinary hesitancy, shy bladder syndrome, DESD, urinary retention, or laryngeal spasm, as well as to monitor the efficacy of treatments for bladder conditions and to assist in the passage of medical devices through bodily sphincters as well as to treat congestive heart failure.

13 Claims, 5 Drawing Sheets

OTHER PUBLICATIONS

Helen Rittenmeyer "Sacral Nerve Neuromodulation (InterStim®) Part I: Review of the InterStim® System", Advanced Clinical Practice, Urologic Nursing, 28 (1) (2008) 15-20.

Hedlund, Petter. "Nitric Oxide/cGMP-Mediated Effects in the Outflow Region of the Lower Urinary Tract-is There a Basis for Pharmacological Targeting of cGMP?" World J Urol (2005) 23: 362-367.

Mamas, Mamas; et al. "Nitric Oxide and the Lower Urinary Tract: Current Concepts, Future Prospects." Urology 61: 1079-85, 2003.

Groat, Willam; et al. "Pharmacology of the Lower Urinary Tract." Annu. Rev. Pharmacol. Toxicol. 2001. 41:691-721.

Bazil, Michelle. "Muscarinic Pharmacology: No Need to Memorize." American Journal of Pharmaceutical Education, vol. 63, Summer 1999.

Zhou, Yuan, et al. "Neuronal Nitric Oxide Synthase in the Neural Pathways of the Urinary Bladder." J. Anat. (1999) 194, pp. 481-496.

Sladden, Michael, et al. "A Community Study of Lower Urinary Tract Symptoms in Older Men in Sydney, Australia." Aust. N.Z.J. Surg. (2000) 70, 322-328.

Toda, Noboru, et al. "Nitric Oxide and Penile Erectile Function." Pharmacology & Therapeutics 106 (2005) 233-266.

Ho, Mat, et al. "Physiologic Role of Nitric Oxide and Nitric Oxide Synthase in Female Lower Urinary Tract." Curr. Opin. Obstet Gynecol 16: 423-429. 2004.

Andersson et al. "Nitric Oxide Synthase and Nitric Oxide-Mediated Effects in Lower Urinary Tract Smooth Muscles." World J Urol (1994) 12: 274-280.

* cited by examiner

NON-INVASIVE MODULATION OF THE AUTONOMIC NERVOUS SYSTEM

CROSS REFERENCE TO RELATED APPLICATIONS

This application claims priority based on U.S. Provisional Application Ser. No. 60/693,122 filed Jun. 23, 2005.

FIELD OF THE INVENTION

This invention relates methods and apparatus for non-invasive modulation of the autonomic nervous system, in particular, the use of heat to modulate the balance between sympathetic and parasympathetic control of muscle tone.

BACKGROUND OF THE INVENTION

Without limiting the scope of the invention, its background is described in connection with novel methods and apparatus for modulation of autonomic system control of muscle activity. The autonomic nervous system controls many vital bodily systems, including the cardiovascular system, gastrointestinal, urinary and bowel functions, temperature regulation, and muscle tone.

The autonomic nervous system is primarily composed of the sympathetic and parasympathetic systems. In certain diseases and conditions, the balance between sympathetic and parasympathetic system control is implicated either causally or in attempted remediation. For example, filling and emptying of the bladder, or "reflex micturition", involves a balance of sympathetic and parasympathetic control. Filling of the bladder requires relaxation of the detrusor muscle of the bladder due to sympathetic stimulation of beta-adrenergic receptors as well as sympathetic stimulation of alpha-adrenegic receptors by norepinephrine causing contraction of the internal involuntary urethral sphincter of the bladder neck.

Conversely, emptying of the bladder is effected when the cortical center of the brain triggers inhibition of sympathetic impulses and stimulates the parasympathetic system to release acetylcholine which results in relaxation of the internal and external sphincters and contraction of the detrusor muscle. Changes to the physiology of the urinary tract as a consequence of aging and which affect continence include decreases in bladder elasticity with reduced bladder capacity resulting in more frequent urination and decrease in strength of the detrusor muscle, resulting in incomplete emptying.

Reflex micturition is implicated in Lower Urinary Tract Symptoms (LUTS), including those caused by prostatic enlargement or Benign Prostatic Hyperplasia (BPH). LUTS is quite common in men as they age. In one study of men aged 40-80, 54% needed to wake up at least once at night to urinate, 47% indicated they had terminal dribbling sometimes or frequently, 30% experienced urgency (although only 4% had urge incontinence), 21% experienced hesitancy, and 19% could retain urine in their bladder during the day for no more than 2 hours. Sladden M J et al. A Community Study of Lower Urinary Tract Symptoms in Older Men in Syndey, Australia, *ANZ Journal of Surgery*, May 2000, vol. 70, no. 5, pp. 322-328(7).

BPH is the most common benign neoplasm in men and can be identified histologically in half of all men at age 60, and in 90% by 85 years. The increase in size of the prostate inside its capsule exerts pressure on the urethra, which passes through the capsule, resulting in obstruction to urine flow. As the prostate enlarges, the gland is forced to press against the urethra in a clamp-like fashion. The bladder wall becomes thicker and irritable and is less extensible thus reducing capacity. The bladder can contract even when it contains small amounts of urine resulting in frequent urination. Ultimately, the bladder weakens and loses the ability to fully empty. Urine retention and strain on the bladder can lead to urinary tract infections, bladder or kidney damage, bladder stones, and incontinence. In the USA, about 25% of men will be treated for BPH by age 80, and over 300,000 surgical procedures are performed each year for BPH (mostly transurethral resection of the prostate, TURP).

In certain cases of hesitancy where the prostate is not significantly enlarged (no prostate disease), excessive sympathetic tone (due to anxiety and other factors) is present. One social anxiety syndrome resulting in inability to relax the urinary sphincter muscles is "paruresis" (a.k.a. shy bladder syndrome, bashful bladder syndrome (BBS), bashful kidneys, pee-phobia, urophobia, and psychogenic urinary retention) is characterized by difficulty in urinating in the presence of others. Individuals with BBS are sometimes referred to as paruretics. This syndrome may affect as much as seven percent (7%) of the US public, or 17 million people, both male and female, and affected individuals may be required to utilize self-catheterization in order to empty the bladder.

In individuals having hesitancy due to excessive sympathetic tone, diminishing the activity of the sympathetic nervous system by α-adrenoreceptor antagonists (alpha blockers) is helpful in treatment. The alpha blocker drugs aim at reducing sympathetic tone of the bladder particularly the neck of bladder. It can also help people with enlarged prostate in whom relaxing the tone of the neck can be useful. Alpha blockers that have been approved for the treatment of symptoms associated with BHP include the drugs terazosin (marketed as Hytrin), doxazosin (marketed as Cardura), tamsulosin (marketed as Flomax), and alfuzosin (marketed as Uroxatral). All of these drugs act to by relaxing the smooth muscle of the prostate and bladder neck to improve urine flow and to reduce bladder outlet obstruction. Terazosin and doxazosin were developed first to treat high blood pressure, while tamsulosin and alfuzosin were developed specifically to treat BPH. The problem with use of alpha blockers is that the entire body is treated to ameliorate a local condition. Each of these drugs can have use limiting side effects.

What is needed are methods and apparatus for modulating the balance between the sympathetic and parasympathetic components of the autonomic nervous system in the treatment of a number of conditions including inducing a rapid anti-sympathetic effect that lasts only long enough alleviate conditions manifest by excessive sympathetic tone, including conditions such as hesitancy during urination and shy bladder.

BRIEF SUMMARY OF THE INVENTION

The present invention is directed to methods and apparatus for use of heat to modulate autonomic system control of muscle activity. The controlled application of heat induces vasodilation by shifting the sympathetic-parasympathetic balance, including through the induced increase in local production of nitric oxide. Therefore, the tolerable heat therapy of the present invention is applied in conditions where increased production of nitric oxide is needed. In one embodiment of the invention methods and apparatus are provided for modulating an activity of a target muscle system in the body by applying heat to reduce sympathetic tone or increase parasympathetic tone in the target muscle system to relieve a symptom of urinary hesitancy, shy bladder syndrome, DESD, urinary retention, or laryngeal spasm. In another embodiment of the invention, the autonomic nervous system is modulated to decrease peripheral vascular resistance in the treatment of heart failure.

In one embodiment in the treatment of urinary hesitancy, heat is used for rapid transient increase in the activity of parasympathetic nervous system. Transient inhibition of sympathetic nervous system activity by heat is effected by application of heat locally (perineal) or systemically specially in areas with maximum sympathetic innervation such as the fingertips.

In one embodiment, the application of heat is short term and designed for acute effects in reduction of urinary hesitancy and increasing urinary flow by inducing muscle relaxation through exposure of the skin to tolerable heat to induce muscle relaxation and help with urination.

In another short term acute indication, the application of heat is designed for acute effects in treatment of urinary retention following catheterization or surgery whereby sphincter relaxation and detrusor contraction is induced through exposure of the skin to tolerable heat to help with urination. In other embodiments, heat is provided by diathermy.

In other embodiments, heat is utilized in conjunction with medical procedures involving the passage of instruments through sphincters and facilitates such passage by dilating the sphincter through a heat induced parasympathetic response induced by local or regional heating.

In certain embodiments, the heat is applied proximal or close to the target muscle system while in other embodiments the heat is applied regionally or even distally to create a systemic anti-sympathetic effect including an effect in the target muscle system. In certain embodiments, the heat is provided by a wearable appliance which may include heatable inserts or pads that are dimensioned for placement in desired anatomical locations including appliances is disposed in, or in association with garments including underwear, garter type belts, gloves, socks, shoes, helmets, scarves, jackets and vests. The apparatus includes a heating element, a heating controller connected to the heating element, and a source of power for the heating element.

In other embodiment, the heat is provided by a non-wearable fixed or portable appliance such as a plumbing or bathroom fixture for delivering heat locally, regionally and/or distally to the target muscle system. The appliance may be adapted to deliver radiant heat, warm air, or a warm hand hold.

Optionally, the heating can be used in conjunction with a pharmacologic approach such as treatment with drugs including alpha blockers, beta blockers, ACE inhibitors, muscarinic receptor agonists, and combinations thereof. In other embodiments, heating is utilized in conjunction with one or more additional non-pharmacologic techniques including controlled audio/visual input, carotid massage, ocular message, and/or stimulation with electric, magnetic, and/or electromagnetic neuromodulating devices used to increase local ANS activity in the target muscle system.

In one embodiment, an apparatus is provided for controllably inducing a carotid sinus reflex that includes at least one pad dimensioned to apply compression to one or both carotid sinuses; and a band for holding the one or more pads against the one or more sinuses. The pad may optionally include a controllable heating element and/or a controllable vibrating element. In other embodiments, apparatus are provided for controllably providing ocular compression and thereby inducing a parasympathetic response for inducing smooth muscle relaxation. The apparatus includes a binocular housing and a pad situated in each housing and dimensioned to apply compression to both eye balls.

In other embodiments, methods and apparatus are provided for relaxing muscles of sphincters such as in the bladder neck by delivering sufficient intraluminal local heating to cause relaxation of the muscles. The intraluminal local heating may be provided by a catheter or cystoscope having at least one heatable section. Alternatively, a parasympathetic stimulus sufficient to cause bladder emptying is provided by implanting a device that is heats differentially in response to RF, electromagnetic, ultrasound or microwave radiation from an external source. By differentially, it is meant the device heats in response to the external stimulation to an extent exceeding the responsive heating of tissue.

In other embodiments, methods and apparatus are provided for evaluating sympathetic over-reactivity, for example through use of a multi-channel heat monitoring device that continuously probes heat at fingertips and/or toes before, during, and after a sympathetic stimulator. In other embodiments, methods and apparatus are provided for evaluating the efficacy of a treatment, including a drug therapy, for urinary hesitancy, as well as for evaluating the effects of treatments by on diuresis and bladder function, by determining a urinary output flow by volume over time.

In another embodiment of the invention, methods and apparatus are provided for use of heat to shift the sympathetic-parasympathetic balance, including through the induced increase in local production of nitric oxide, in order to induce vasodilation and reduced resistance to peripheral blood flow in the treatment of symptoms of heart failure. The heat is provided by a wearable appliance or garment such as underwear, gloves, socks, shoes, helmets, scarves, jackets, vests and body suits.

BRIEF DESCRIPTION THE DRAWINGS

For a more complete understanding of the present invention, including features and advantages, reference is now made to the detailed description of the invention along with the accompanying figures:

FIGS. 1A and B illustrate embodiments of the invention including placement of a heating element on the perineum. In FIG. 1A, the device can be a independent of a garment. In FIG. 1B, the perineal heating element is shown as held in position by, or incorporated as part of, a garment.

FIG. 2A-F depict various areas where heat can be locally and regionally applied for parasympathetic modulation of the bladder.

DETAILED DESCRIPTION OF THE INVENTION

Figure 1A:
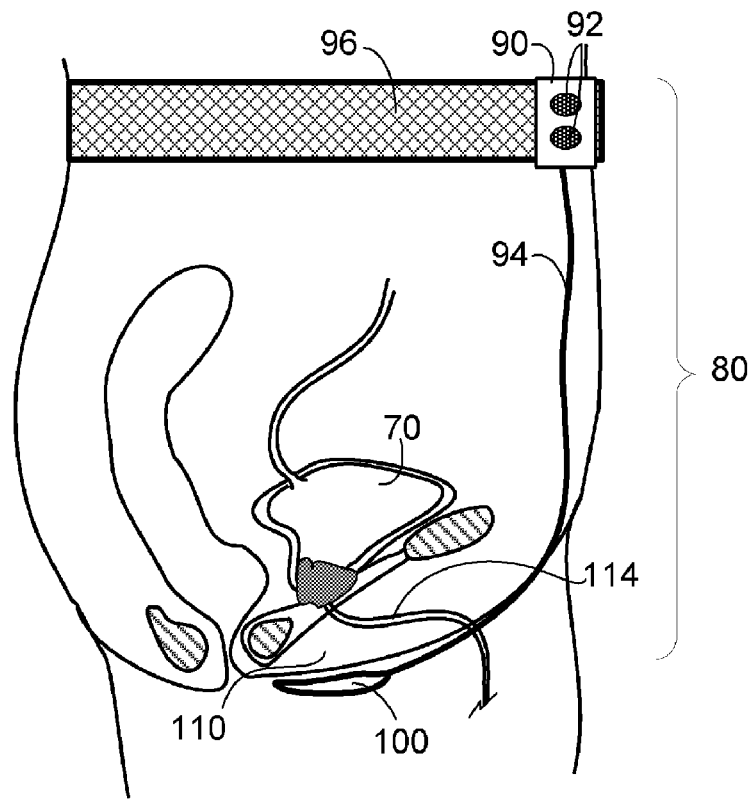
Figure 1B:
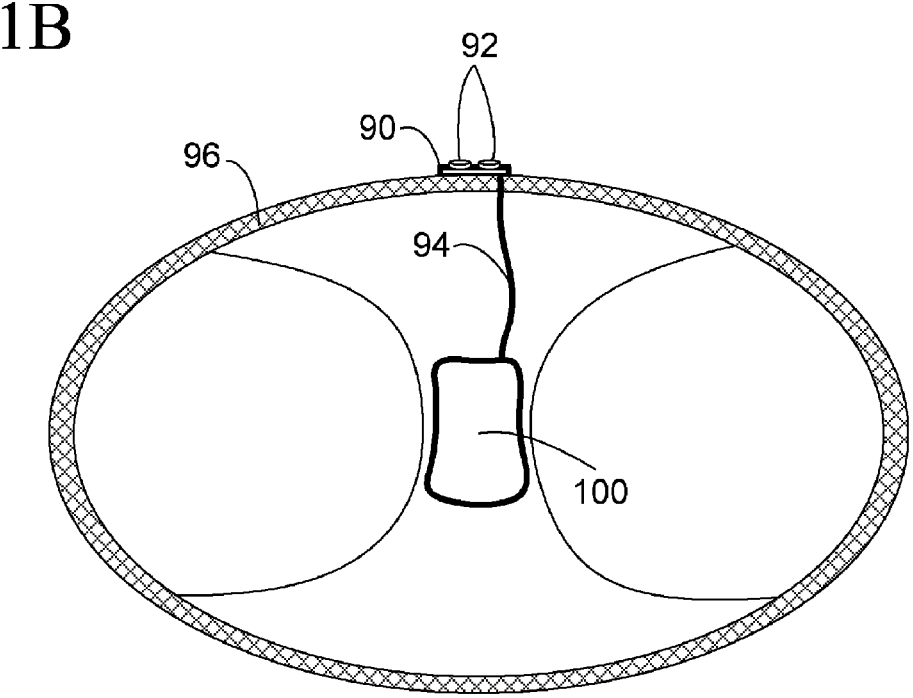

This invention discloses methods and means to reduce sympathetic stimulation or increase parasympathetic stimulation in order to modulate the activity and performance of desired smooth muscle cells in the body. The muscle cells can be in sphincters like the bladder neck sphincter, sphincter of the anus/rectum, and the ciliary sphincter in the eye. The muscle cells can also be the smooth muscle cells of the pre-capillary sphincter-like arterioles (a.k.a. arteriole sphincter band of smooth muscle at each capillary entrance) and the smooth muscle wall of luminal organs like the intestines.

As disclosed herein, methods and apparatus are provided for heating or increased local and/or regional warming to reduce sympathetic tone or increase parasympathetic tone as needed. In accordance with the invention, heat is used in at least two ways: in one embodiment local heat creates local anti-sympathetic effects partially mediated by nitric oxide, while in another embodiment heat is used to stimulate regional or systemic parasympathetic reflex responses such that heat applied distally creates an anti-sympathetic effect in a target tissue.

As disclosed herein, a heat may be combined with non-pharmacologic techniques for modulating ANS, mostly for regional and transient modulation based on anatomical reflex zones. These non-pharmacologic techniques may include non-invasive electric, magnetic, or electromagnetic neuro-modulating devices used to increase local ANS activity. In other embodiments, pharmacologic approaches are combined with heating, the heating permitting lower dosages with reduced side effects.

While the making and using of various embodiments of the present invention are discussed in detail below, it should be appreciated that the present invention provides many applicable inventive concepts which can be employed in a wide variety of specific contexts in which modulating the sympathetic-parasympathetic balance is desired. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

ABBREVIATIONS: The following abbreviations are used throughout this application:
ACh Acetylcholine
ANS Autonomic Nervous System
BHP Benign Prostatic Hyperplasia
CSH Carotid Sinus Hypersensitivity
(L-NAME) $N^G$-nitro-L-arginine methyl ester (NO synthase inhibitor)
LUTS Lower Urinary Tract Symptoms
NO Nitric Oxide
NOS Nitric Oxide Synthetase
PAT paroxysmal atrial tachycardia
SBS Shy Bladder Syndrome,
SNP sodium nitroprusside The phrase "urinary hesitancy" refers herein to difficulty commencing the flow of urine or slowed or delayed start of the urinary stream.

A "sphincter" is a circular muscle that normally maintains constriction of a natural body passage or orifice and is capable of relaxation as required for normal physiological functioning. There are a number of different sphincters in the human body, examples of which include: the two sphincters of the anus, the cardiac sphincter at the upper portion of the stomach, the pyloric sphincter at the lower end of the stomach, the urethral sphincter controlling emptying of bladder, the sphincter of Oddi (a.k.a. Glisson's sphincter), which controls secretions from the liver, pancreas and gall bladder into the duodenum and the ciliary sphincter in the eye. The phrase "precapillary sphincter" or "arteriole sphincter" refers to the band of smooth muscle at the junction of arterioles and capillaries and thus at each capillary entrance.

The phrase "diathermy" means the controlled production of deep heating beneath the skin in the subcutaneous tissues, deep muscles and joints for therapeutic purposes. Current diathermy devices on the market generate deep heating by using radio (high) frequency, microwave or ultrasonic energy. Current ultrasonic diathermy devices operate in a frequency range of 0.8 to 1 MH Z and generate heat by acoustic vibration. Radio frequency (r.f.) diathermy is assigned an operating frequency of 27.12 MH Z (short wave) by the Federal Communications Commission. Microwave diathermy is assigned 915 MH Z and 2450 MH Z as operating frequencies (these are also Microwave oven frequencies). The present informal position of the Food and Drug Administration is that a diathermy device should be capable of producing heat in tissue from a minimum of 104° F. to a maximum of 114° F. at a depth of two inches in not more than 20 minutes. RF heating can be done by dielectric or inductive methods and the physical configuration of the device is designed in accordance with electrical engineering principals depending on the ultrasound, MW or RF method desired.

As used herein, the term "wearable appliance" includes heatable inserts or pads that are dimensioned for placement in desired anatomical locations, including stand-alone appliances, appliances disposed in garments, and appliances that are used in association with a garment. Appliances that are used in association with a garment include appliances that are worn inside and those that are worn outside of the garment. Wearable appliances also include applicants that may be dimensioned to be carried, such as for example, a hand-warmer for a pocket. As used herein, the term "non-wearable" appliance includes fixtures and/or portable devices that may be placed in a bathroom or facility but are not dimensioned to be attached or carried by an individual during ambulation.

As used herein, "proximal" means nearest or closest to. Thus, areas and tissues proximal to the bladder include the perineum and pubic areas in addition to the detrusor muscles and the muscles of the bladder neck. Regional or local means in the general vicinity. Thus, as used herein "local" heating of the bladder may include heating of areas proximal to the bladder and further may include heating in the groin, lower abdomen and upper inner thigh areas. "Distal" in the context of the present invention means the opposite of proximal and means at a distance apart from the structure described. Areas distal to the bladder include, for example but without limitation, the face, hands and feet.

As used herein, the phrase "when desired" means surrounding the time at which the relevant function is desired.

In response to variations in environmental phenomena including temperature, food intake, and stressful experiences, afferent nerves from both systems convey impulses from organs, muscles, the circulatory system and the periphery of the body to controlling centers in the medulla, pons and hypothalamus of the brain. From these centers, efferent impulses are conveyed to all parts of the body by the parasympathetic and sympathetic nerves. Typically, these responses are largely involuntary automatic or reflex responses.

Parasympathetic system impulses are conveyed through cranial nerves number 3, 7, 9, and 10 (vagus nerves), in addition to some sacral nerves. Sympathetic impulses are conveyed down the spinal cord to sympathetic nerve bodies (ganglia) alongside the spine from which impulses travel to other nerve bodies (or neurons) in pathways that are in conjunction with blood vessels. Both sympathetic and parasympathetic systems include two groups of motor neurons:

preganglionic neurons, arising in the CNS, and running to ganglions where they connect via synapses to postganglionic neurons, which run to effector tissues and organs.

Acetylcholine (ACh) is the neurotransmitter of the preganglionic sympathetic neurons. Release of ACh stimulates action potentials in the postganglionic neurons, which ultimately release the neurotransmitter noradrenaline (a.k.a. norepinephrine). Noradrenaline is excitatory is some cases and inhibitory in others. Thus, the release of noradrenaline stimulates increase in heartbeat and blood pressure, dilation of pupils and trachea and bronchi, conversion of glycogen into glucose in the liver, shunting of blood from the skin and viscera to the skeletal muscles, brain, and heart, inhibition of gastrointestional peristalsis and inhibition of contraction of the bladder and rectum. In opposition to the effects of the sympathetic system, parasympathetic stimulation causes slowing down of the heartbeat, lowering of blood pressure, constriction of the pupils, increased blood flow to the skin and viscera, peristalsis of the GI tract and contraction of the bladder. As with the sympathetic system, ACh is also the neurotransmitter for presynaptic parasympathetic neurons. In contrast, ACh is also the neurotransmitter for many postganglionic parasympathetic neurons. However, some postganglionic neurons release nitric oxide (NO) as their neurotransmitter. In such neurons, NO is formed by the NOS mediated conversion of L-arginine to citrulline. Once produced, NO is a highly diffusible agent able to elicit effects relatively far from the site of production. As a consequence of diffusion, the source of NO is a determinant of its concentration and a major factor determining the biological effect. At low concentrations, the direct effects of NO predominate. The principal direct effect of NO is the activation of soluble guanylate cyclase to increase levels of cyclic guanosine 3'5'-monophosphate (cGMP). The cGMP acts as a second messenger to induce relaxation via modified activity of protein kinases, phosphodiesterases (PDEs) and ion-channels that regulate contractile protein activity.

Nitric oxide is the primary neurotransmitter responsible for smooth muscle relaxation in the lower urinary tract and is thus a critical mediator in regulating bladder function. Nitric oxide synthetase (NOS) containing parasympathetic neurons that cause relaxation upon stimulation densely populate the prostate, urethra and bladder. However, the density of NOS containing nerves is highest in the outlet region or neck of the bladder. During emptying of the bladder, or voiding, cholinergic parasympathetic nerves induce relaxation of the smooth muscle of the bladder neck and proximal urethra.

Nitric oxide (NO) has been shown to be involved in cutaneous active vasodilation induced by systemic application of heat on the basis that local inhibition of NO synthetase resulted in inhibition of cutaneous local perfusion while local perfusion of the NO donor, sodium nitroprusside, resulted in maximum local cutaneous perfusion. See D L Kellogg Jr., C G Crandall, Y Liu, N Charkoudian, and J M Johnson. "Nitric oxide and cutaneous active vasodilation during heat stress in humans" *J Appl Physiol* 85 (1998) 824-829. Similarly, it was found that NO mediates vasodiliation in response to local application of heat. See D L Kellogg Jr., Y Liu, I F Kosiba, and D. O'Donnell. "Role of nitric oxide in the vascular effects of local warming of the skin in humans" *J Appl Physiol* 86 (1999) 1185-1190. Conversely, local cooling induces cold-sensitive afferent nerves to activate sympathetic nerves to release norepinephrine, which leads to local cutaneous vasoconstriction. J M Johnson, T C Yen, K Zhao, and W A Kosiba. "Sympathetic, sensory, and nonneuronal contributions to the cutaneous vasoconstrictor response to local cooling" *J Physiol Heart Circ Physiol* 288 (2005) H1573-H1579.

In accordance with the present invention, heat is used as a treatment for rapid or transient reduction of sympathetic nervous system activity or increasing the activity of parasympathetic nervous system in various medical conditions where shifting the balance towards lower sympathetic nervous system activity is desired. The heat can be local or generalized (systemic), transient or long term.

In one embodiment of the invention, pharmacologic (drug) approaches are combined with heating. However, in this combination, the drugs expected to be effective at a lower dosages than they are given for their primary indication, thereby reducing side-effects. The alpha blocker drugs ($\alpha$-adrenoreceptor antagonists), which reduce sympathetic tone of the bladder particularly the neck of bladder, may be particularly useful in combination with heat therapy. Alpha blockers including terazosin (marketed as Hytrin), doxazosin (marketed as Cardura), tamsulosin (marketed as Flomax), and alfuzosin (marketed as Uroxatral) are already approved for BHP. Other potentially useful drugs include angiotensin converting enzyme (ACE) inhibitors and beta-adrenergic receptor blocking agents ($\beta$ blockers) such as propranolol (Inderol), which reduce excessive sympathetic activity.

Medications that produce the same effects as the parasympathetic nervous system are called "cholinergic drugs" because they produce the same effects as acetylcholine, which is the most common neurohormone of the parasympathetic nervous system. Examples of direct acting cholinergic drugs that are expected to favor parasympathetic type relaxation for purposes of relaxation of the neck of the bladder include agonists of muscarinic receptors, which are principally responsible for smooth muscle stimulation. Muscarinic receptor agonists that cause parasympathetic over activity include choline esters such as bethanechol chloride (Urecholine®, orally available agent with fewer cardiovascular effects and longer-half-life), arecoline (also an agonist of nicotinic receptors), carbachol (i.e. Miostat®, some nicotinic activity, typically used to treat glaucoma). Clinically available alkaloids that are direct muscarinic receptor agonists include pilocarpine (i.e. Akarpine®, muscarinic selective agent typically used to treat glaucoma).

Examples of indirectly acting cholinergic drugs that function as muscarinic receptor agonists (act by inhibiting acetylcholine esterase, thereby reducing the destruction of acetyl choline) include ambenonium chloride (Mytelase), edrophonium chloride (Tensilon), and piridogstimina (Mestinon), neostigmine (Prostigmine) and physostigmine. In one embodiment, topical sensory nerve blockade by an anesthetic cream may also be employed to encourage vasodilation and parasympathetic relaxation.

In another embodiment of the invention, heat treatment is combined with other non-pharmacologic methods for decreasing sympathetic tone and increasing parasympathetic tone including e.g. mental relaxation, ablation of light, sound and all other established methods. In one embodiment, the specialized heating devices are combined the training exercises such as yoga exercise and biofeedback. In other embodiments, sensory input is provided to the ANS including audio visual input such as via a head set or helmet that blocks sympathetic stimulating audiovisual input from the environment and creates instant relaxation. The head set can be adapted to provide relaxing audio input (including the sound of running water) and/or reduced light. Such a head set or helmet may be provided with heating capability specially for gentle heating the ears which are heavily innervated by sympathetic nerves. It is anticipated that individual requirements for attaining a desired level of ANS modulation will vary widely. Thus, a combination of approaches may be required for certain individuals with high adrenergic activity, including heating in addition to one or more of: controlled audio/visual input, pharmacologic treatment, and stimulation by electric, magnetic, or electromagnetic devices. In one embodiment, a whole or partial body suit is provided with multiple heating regions to modulate the ANS to reduce sympathetic activity. Patients with severe cases of ANS imbalance may benefit from using this on a chronic or periodical basis. It can be used an alternative for rapid reduction of anxiety in clinical settings. A combination with pharmacologic methods may be chosen by physicians or medical professional.

Further non-pharmacologic approaches for modulating ANS are combinable with the heat therapy disclosed herein. These approaches are mostly for regional and transient direct stimulation of the nervous system but also include systemic applications. These non-pharmacologic techniques may include electric, magnetic, or electromagnetic devices, including those adapted for local electrical or magnetic stimulation of desired nerves including the sacral nerve. Stimulation is modulated and tuned in the individual patient to increase parasympathetic rather than sympathetic responses in conjunction with heat therapy.

The following examples are included for the sake of completeness of disclosure and to illustrate the methods of making the compositions and composites of the present invention as well as to present certain characteristics of the compositions. In no way are these examples intended to limit the scope or teaching of this disclosure.

Parasympathetic Stimulation of the Urinary Tract: In one embodiment of the invention, methods and apparatus are provided for using heat to stimulate the parasympathetic nervous system to release the neck of the bladder and permit emptying of the bladder for relief of urinary hesitancy, shy bladder syndrome, DESD, and urinary retention.

Efferent and afferent nervous pathways innervating the lower urinary tract include three sets of peripheral nerves, the sacral parasympathetic traveling through the pelvic plexus, the thoracolumbar sympathetic traveling through the sympathetic chain ganglia, and the sacral somatic or pudendal nerves. Sympathetic pathways mainly inhibit the bladder by relaxing contraction of the detrusor and simulating contraction of the urinary sphincters. Voiding involves suppression of the sympathetic pathways and stimulation of the parasympathetic pathways which provide excitatory input to increase ureteral peristalsis, cause contraction of the detrusor muscle of the bladder, and relax the sphincters of the bladder neck. The somatic pathways principally innervate the external urethral muscles.

In one embodiment, temporary inhibition of, or reduction in, sympathetic tone is applied to the treatment of urinary hesitancy. The same applies to reducing urinary retention (residual urine in the bladder). Urinary retention has been associated with poor outcomes including urinary tract infections. In one embodiment, local heating is provided in one or more areas of the groin and/or perineum for stimulating the local production of NO which then acts locally and transiently to stimulate contraction of the detrusor muscles of the bladder and to relax the smooth muscle cells of the bladder neck and help further open the neck to reduce urinary hesitancy, increase urinary flow, and decrease the residual urine in the bladder.

The methods for relaxation by heating/warming include using gentle heat increasing in intensity up to the point of maximum tolerance which results in relaxing muscles. In certain embodiments, local heat to the pubic area, groin and/or perineum is provided through a wearable appliance such as a garment that provides local and/or regional heat on demand when the individual wishes to empty their bladder.

In one embodiment, the noninvasive heatable device is dimensioned for placement at a location that will effect heating at a target body to induce local relaxation. The target body can be any sphincter in the body that is innervated by sympathetic nerves, such as for example the bladder neck. In one embodiment the heating method is conventional such as by electric heating coils or is provided by ultrasound, microwave (MW) and/or radio frequency (RF) energy. In particular, in one embodiment ultrasound, microwave (MW) and/or radio frequency (RF) diathermy is employed to generate deep heating up to 2 inches from the skin surface without damage to the skin. Ultrasound diathermy applies high-frequency acoustic vibration to tissues, while MW diathermy applies a strong electrical field with comparatively low magnetic-field energy to induce intra-molecular vibration of highly polar molecules within the treated tissue to generate a thermal effect. RF diathermy involves application of shortwave length, high-frequency electromagnetic fields. The electromagnetic field can be perpendicular or longitudinal in orientation. Although perpendicular electromagnetic field devices have been historically utilized in medical RF diathermy devices, devices able to low-energy longitudinal fields are also available (i.e. Selicor Brand Selitherm devices) and are applicable to the present invention.

In one embodiment of the invention, the heating is provided by Far Infrared Radiation. Commercially available versions of such elements able to provide heat to subcutaneous tissue include, for example, Far Infrared (FIR) Radiant Heating elements. (Challenge Carbon Technology Co., Taiwan). Such elements are suited for FIR heated clothing due to their flat form and foldable, durable and washable properties. The elements as provided for use in clothing include lithium-ion batteries, temperature controller and OCP (Over-Charge Protector) integrated in one controller that provides for rapid heat up according to set upper levels.

In one embodiment of the invention heating is electromagnetic based and is effected by selectively heating a component of the device such as a metal compound. Alternatively the component may be a compound sensitive to heating by ultrasound, such as for example, polymers selectable by those of skill in the art to heat up preferentially by ultrasound. The polymer will preferably have the characteristic that its acoustic impedance exceeds that of surrounding tissue thus preferentially heating the polymer component. Examples of useful polymers in this regard include silicone, polyvinylchloride, nylon, polyurethane and combinations thereof that optimize the heating rate or to useable properties such as flexibility and stability. In this embodiment, one or more layers or inserts of the polymer component are heated by a remote or local ultrasound transducer.

In the case of heating the groin area, and as depicted in FIGS. 1A and B, the wearable product 80 can be heating underwear or a device that can be placed in ordinary underwear. Wearable product 80 can include a power supply 90 and on-off controls 92. The controls 92 and power supply 90 are connected to heating element 100 by one or more leads 94. Warming is controlled and increases progressively until it reaches a threshold of tolerance or the desired effect is obtained. The device controller provides for maximum temperature settings such that a patient can turn the device on and warming will increase progressively until the maximum is reached and will hold steady at this temperature until turned up, down or off.

FIGS. 1A and B depicts one embodiment of a heating device wherein heating element 100 is dimensioned for placement against the perineum 110 of the patient such that heat generated affects tissues near the urethra 114 and thereby provokes a parasympathetic release of NO with attendant relaxation of smooth muscle of the urethra such that emptying can occur from the bladder 70. In one embodiment, the device is worn in association with, or disposed in, underwear, which as used herein includes garters, stockings, athletic supporters and girdle type garments.

The device located therein can heatable via combustible energy sources such as butane or propane heaters, electric energy, electromagnetic energy (infrared radiation). Power can be delivered through a wearable power supply and cause heat on demand.

Figure 2:
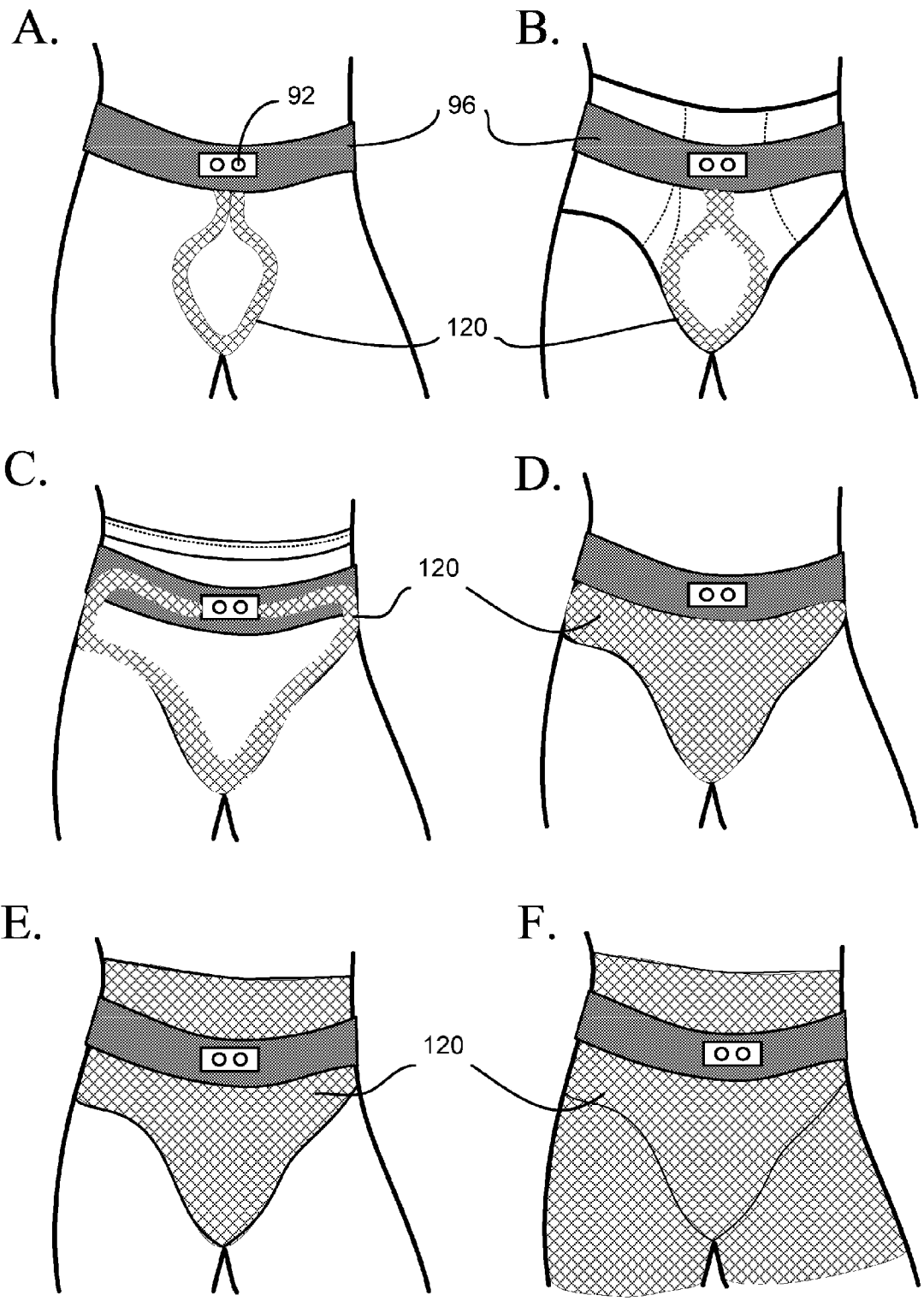

A variety of other wearable devices are envisioned in accordance with the present invention including, for example, embodiments depicted in FIG. 2. In FIGS. 2A and B, devices particularly suitable for male patients are provided that avoid application of heat to the testes. The device can be a standalone device as in FIG. 2A, or can be incorporated into a garment as in FIG. 2B. Other of the embodiments of Figures C-F may be used in either males or females. The garment can be provided with various openings as may be desirable. In each of the embodiments of FIG. 2, the heatable area is depicted with crosshatching 120. In each of the depicted embodiments, local heat to the groin and/or perineum is provided through the wearable appliance such as a garment that provides local and/or regional heat on demand when the individual wishes to empty their bladder. In one embodiment, a form of wearable device can include a belt or an elastic band around stomach that can have a cosmetic function as well. In one embodiment, an over-underwear elastic wearable heating cloth is provided that is composed of a stretchable mesh. Wearing the heating cloth over regular underwear provides certain sanitary advantages.

In other embodiments, a systemic parasympathetic response is provided by heating at sites of the body that are removed from or "distal to" the area of the body in which parasympathetic relaxation of smooth muscle is desired. Distal heating provided, for example to the hands or areas thereof, stimulates a reflex parasympathetic response that transits through the central nervous system and back down to reduce sympathetic signaling and provide a parasympathetic stimulus for contraction of the detrusor muscles of the bladder and to relax the smooth muscle cells of the bladder neck and help further open the neck to reduce urinary hesitancy, increase urinary flow, and decrease the residual urine in the bladder. In one embodiment the application of distal heat is provided by wearable products and appliances that may include garments having embedded heating elements such as heating underwear, gloves, socks, shoes, helmets and jackets as well as heatable inserts or pads that are dimensioned for placement in any of the above garments.

In one embodiment, the heating elements embedded in wearable garments and/or inserts are designed for: 1) placement based on the sympathetic/parasympathetic map on the body such that heat is concentrated on local and regional areas to modulate autonomic nervous system to relax targeted muscles, as opposed to generalized heating of the whole body, and 2) is on-demand and aimed at short term local relaxation rather than general systemic relaxation.

In one embodiment of the invention, the distal heating apparatus is a glove or portable handwarmer. The device can be dimensioned for carrying in a pocket or purse. The heating applied to the distal area must be of sufficient magnitude to cause the same increase in parasympathetic response as could be obtained by local heating. The optimal site for heating, as well as the intensity and duration of heating, can be readily determined for a given individual based on whether or not the desired relaxation is obtained.

In another embodiment, heating is available from non-wearable appliances. For an example involving fixtures that located in the bathroom, heated hand holds or hand grips are provided for immediate delivery of heat to the hand including the palm and/or fingertips. The heated hand holds are situated to be reachable from an individual using the toilet. In one embodiment, the plumbing for a public bathroom is designed such that the hot water running in bathroom pipes is directed in a serpentine manner through hand holds in proximity to each toilet. Depending on the temperature of the building hot water, the hand holds may be covered with a thin insulating layer to avoid a dangerously hot surface temperature. In another embodiment, provision of heat is quickly on-demand through valves in the case of fluid heat sources and via switches in the case of electric heat sources. It is anticipated that heaters suitable for use in private places will not be limited by the need to make use in apparent to third parties.

In another embodiment, heat is delivered by an air blower or infrared lamp that delivers local heat to a person to stimulate a parasympathetic response and relaxation of the smooth muscle of the urinary neck. The air blower or infrared lamp is aimed to deliver heat to the groin region and is located in immediate proximity to the toilet or urinal, thus becoming a component of a "toilet system." In another embodiment, heat is provided locally through heating elements attached to the toilet and designed to direct heat to the groin, pubis and/or perineum when activated individually by the individual in need of parasympathetic stimulation. In another embodiment, infrared heaters and/or warm air blowers are situated in proximity to the toilet to direct heat to the hands, face, neck and/or torso with sufficient heat and force to induce a systemic parasympathetic effect by distal heating. The temperature and force should not be so aggressive as to induce an adverse sympathetic response. The heating apparatus in the bathroom has to be designed in such a way to minimize any adverse or associated factors that can create or exacerbate anxiety and induce sympathetic surges. For example, heating with a hot-air-blower that is noisy can make it obvious to third parties that the individual is suffering from hesitancy or SBS, the thought of which can worsen the situation for the individual. In light this principle, multiple designs are envisioned for public bathrooms using IR heat radiation, electric heaters, and heated hand holds that can be turned on and off without raising awareness in the surrounding area.

In one embodiment, whether local or distal administration of heat is chronic, regular or periodic for sustained reduction of intraluminal pressure of the bladder neck. For example, the individual patient may schedule a pattern of heating, such as for limited periods 5-10 times a day for reduction of intraluminal pressure of the bladder neck, in the treatment of urinary hesitancy, urinary retention and in Shy Bowel Syndrome. Depending on responses desired and obtained in the individual patient, the intensity and duration of heat can be tuned for optimal responses.

In another embodiment, parasympathetic stimulation is delivered through inhalation, such as inhalation of warm air. Certain areas in certain people can be more sensitive. For example heating facial skin may result in a more prominent effect than heating an arm in certain individuals and the delivery heat can be tested in various locations and then subsequently applied where most efficacious. For distal heating the duration of heating will typically be longer to arouse a systemic response than local heating in the groin, public and perineal areas. In both situations the intensity has to increase up to the comfort boundaries and should not rise to the level where it becomes a stressful stimuli that triggers sympathetic activity.

Treatment of DESD: In some patients with spinal cord injuries, particularly suprasacral injuries, when bladder emptying is attempted, the urinary sphincter contracts along with the bladder. This is termed detrusor-external sphincter dyssynergia (DESD) and results in failure of bladder emptying, often resulting in bladder infection as well as high bladder pressure which can result in hydronephrosis and loss of kidney function. Alpha blockers have not been useful in reducing bladder pressure in DESD and there remain no effective drug treatments. The only surgical treatment is sphincterotomy, which is associated with significant problems and is often ineffective. Delivery of NO by oral or sublingual administration or delivery of NOS encoding genes to the muscle cells of the urethra has been proposed in the treatment of DESD. Mamas M A, et al. Nitric Oxide and the Lower Urinary Tract: Current Concepts, Future Prospects. *Urology* 61 (2003) 1079-85. In one embodiment of the present invention, heat is utilized to stimulate the local release of NO in the neck of the bladder and proximal urethra in the treatment of DESD.

Treatment of Shy Bladder Syndrome: In another indication, the application of heat is designed for acute effects in treatment of shy bladder whereby sphincter relaxation and detrusor contraction is induced through exposure of the skin to tolerable heat to help with urination. Avoidant paruresis can start at any age and affects mainly boys or men, although girls and women can also suffer from it. It has been estimated that one in ten Americans suffers to some degree from "bashful bladder" syndrome, the chronic inability to use a public bathroom when nature calls. The disorder, which appears to run in families, ranges in severity. In mild cases, the affected individual requires the use of a stall instead of a urinal. Moderate cases are able to relieve themselves only in a stall and when the bathroom is empty, while severe cases are unable to urinate no matter how private the surroundings. As a result, the disorder can force many otherwise healthy people to become practically housebound. In some instances, sufferers have bought homes close to their work so they could go home whenever they needed to urinate. Existing therapies include social conditioning and drug therapy with sedatives, anti-anxiety drugs and antidepressants, as well as with alpha-adrenergic blockers and with parasympathetic nervous system stimulants such as bethanechol.

In one embodiment of the present invention, either local or distal heating is employed to lower the resistant threshold that prevents urination. Use of heat therapy for reducing sympathetic surge as disclosed here can be used alone or in combination with existing anti-anxiety therapies as needed.

Local Heating for and by Insertable Medical Devices: In one embodiment of the invention, a local heating device for use in hospital settings is provided for modulation of parasympathetic balance for insertion of medical devices through sphincters. For example, heat is applied to the lower abdomen to induce a parasympathetic relaxation of the urinary sphincter prior to insertion of a catheter into the bladder. Alternatively, the device itself may be designed to deliver local heating, such as for example a heating aspect associated with urinary tubes. Heating induces relaxation of the sphincter such that reduced force is required to pass the device through the sphincter. Thus, there is reduced risk of perforation and the procedure causes less discomfort to the patient. In one embodiment, heat is employed locally or regionally to relax sphincter muscles. For example, for insertion of devices including Foley type catheters, cytoscopes, and stone removal devices, into the bladder or up into the urethra, heat is applied to the groin and lower abdomen prior to insertion of the device. In other embodiments, the device itself is heated or heatable. In one embodiment for the assisting in the insertion of medical devices, heating is provided by diathermy.

Figure 3:
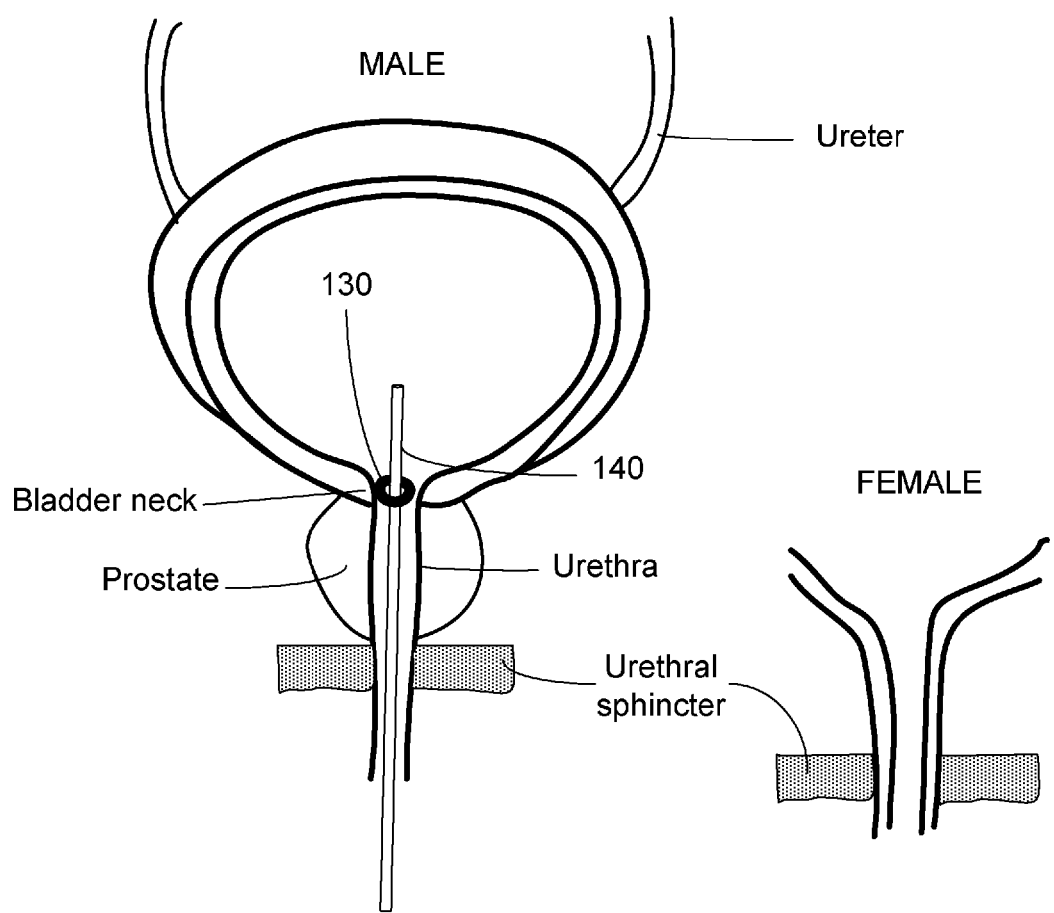
FIG. 3 depicts a urinary catheter having a heatable section for parasympathetic modulation of the sphincter of the bladder neck.

In one embodiment, a device is dimensioned to deliver local heating from inside a fluid passageway such as the urethra and or the ureter, such as for example a heating aspect associated with urinary tubes. In other embodiments, transdermal, transluminal, or local radiation is delivered, including focused heat such as ultrasound or microwave heat. In one embodiment, heat is delivered through radiation but the target organ includes a substance or device for differential absorption of the heat/radiation. For one non-limiting example, in the case of urinary tubes or cystoscopes, a small metal ring or band 130 of material that can be differentially heated is embedded in or on the tube or catheter 140 at a location where it will engage the relevant sphincter such as for example the neck of bladder as shown in FIG. 3. The heatable material is heated noninvasively by RF or electromagnetic radiation that is absorbed by the metal or other differentially heatable compound such as a polymer. The implanted device may alternatively include one or more layers of a polymer composition that is sensitive to heating by ultrasound. Certain polymers that have the property of being preferentially heatable include silicone, polyvinylchloride, polyurethane, nylon, phosphorylcholine and combinations thereof that may optimize the heating rate of the coating or to improve stability or biocompatibility of the coating.

In another embodiment, a differentially heatable implant is dimensioned for insertion and placement proximal to the bladder, such as against a detrusor muscle, the bladder wall or the neck of the bladder is provided. The implant heats differentially in response to RF, electromagnetic, ultrasound or microwave radiation from an external source. The radiation source is activated when emptying of the bladder is desired and the local heating stimulates a parasympathetic response that allows for emptying of the bladder. Once again the heat level must avoid that which would be sufficiently stressful as to elicit sympathetic surges. The level of stress is determinable by the subject's s comfort zone. In any event, the local temperature elicited must be less than what would cause tissue injury or irreversible damage.

Pre-treatment Assessment of Conditions: In one embodiment, methods and apparatus are provided for evaluating the intensity of sympathetic over-reactivity. In one example, a multi-channel heat monitoring device continuously probes heat at the fingertips and/or toes before, during, and after a sympathetic stimulator such as, for example, a mental challenge test or a cold exposure. This device and method distinguishes the hyper-adrenegic component of hesitancy in males who might have both BPH and spastic (hyperactive) bladder neck.

Figure 5:
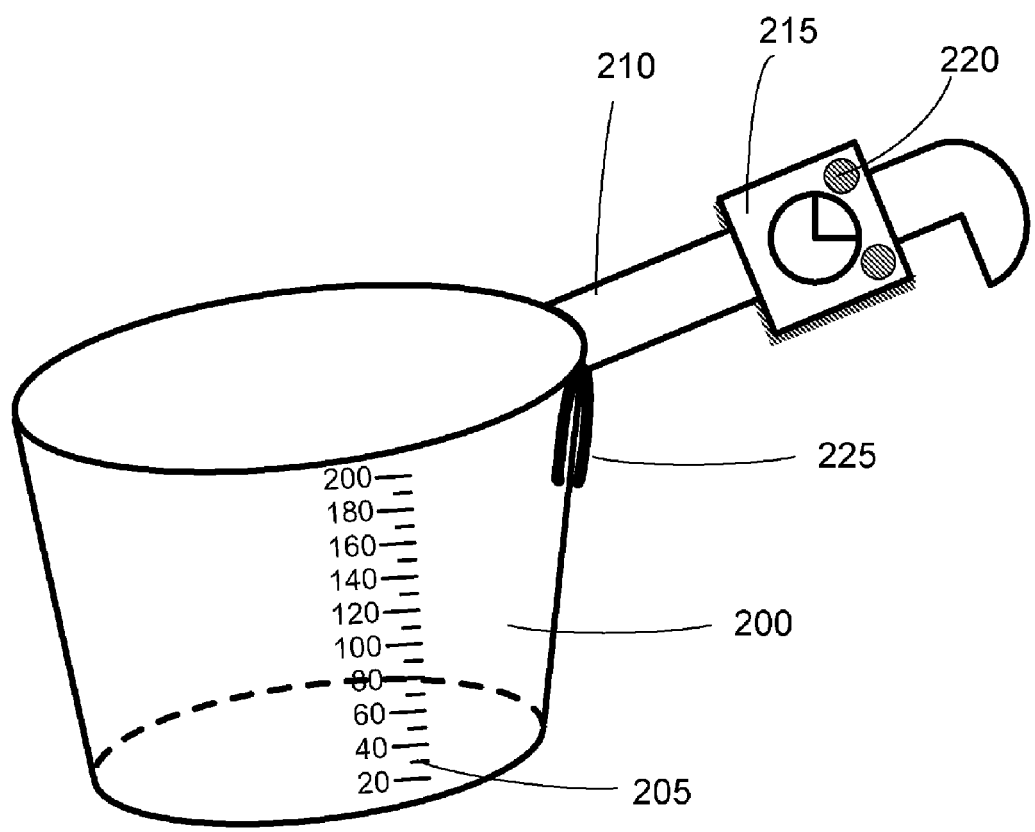
FIG. 5 depicts an example of system for determining urinary output flow by volume over time.

Monitoring Effects of Treatment for Urinary Hesitancy: In one embodiment, an example of which is in FIG. 5, a urine collection container 200 marked with volume scales 205 is provided together with a timer, such as a stopwatch type of timer, allowing the user to measure his or her urinary output flow by volume over time. As depicted, an oval or oblong container shape with a handle 210 may be desirable for collection in a sitting position. The handle may be mounted with a timer 215 having on and off buttons 220 that are pressed when the person starts and stops voiding as well as a display of elapsed time. The total volume over time is used as a measure of functional obstruction at the bladder neck. In one embodiment, a disposable or reusable plastic container to collect urine is configured with a handle 210 for conveniently holding the container in position. Where a disposable or otherwise removable container is desired, the handle may be configured with a clip 225 for affixing the handle to the container. Alternatively, where the disposable container is flexible, such as a bags that are dimensioned for collection and volume measurement of urine, the handle may include a ring that holds the bag. Different designs for collection by males and females may be employed in accordance with anatomical variation.

In one embodiment, a kit is provided for quantitative self evaluation of efficacy of a treatment for urinary hesitancy, the kit including a graduated container for measuring urination volume, a timing device having a start button and a stop button, and a log for recording urination volume over urination time. Such a kit is particularly suitable for evaluating the results of treatment in clinical trials of new therapies for urinary conditions.

Treatment of Nocturia: In one embodiment of the invention, methods and apparatus for treatment of nocturia (voiding during the night) are provided. Nocturia is a common problem in the elderly who have high residual volume in their bladder after voiding. In accordance with the present invention, local or distal heating of sufficient intensity and duration to induce a parasympathetic response is employed before going to bed in order to reduce the residual urine in the bladder and thereby reduce the frequency of voiding during the night. In one embodiment, diathermy is employed to relax the neck of the bladder and to stimulate contraction of the bladder to facilitate full emptying. In one embodiment, the heating device is installed in the home bathroom such that it can be readily employed prior to going to bed. Also more specifically, this method and apparatus is of particular advantage in individuals who experience a significant adverse effect due to pharmacologic treatments of hesitancy and frequency such as hypotension, dry ejaculation, etc.

Treatment of Laryngeal Spasm: Laryngeal spasm is a persistent contraction of the larynx muscles (voice box) such that the vocal cords to come together. The spasm can result in partial or complete blockage of the entrance to the trachea (windpipe). In one embodiment of the invention, noninvasive use of heat, including local, regional and systemic (reflex based) heat, is use to reduce the tone or spasm of laryngeal muscle. The local heating can be administered by a device either self mounted on the neck by the patient for intermittent or chronic use, or as fitted in position by a medical professional. The heat can be focused or concentrated for deep tissue heating (like with ultrasound or microwave) deep enough to reach the muscles (1-3 inches).

Manipulation of the Carotid Sinus Reflex: In one embodiment, the non-pharmacologic modulation of the ANS involves methods and apparatus for placing controlled pressure on the carotid to manipulate the carotid sinus reflex, which plays a central role in blood pressure homeostasis. Baroreceptors associated with the carotid sinus or bulb, which is located at the bifurcation of the internal and external carotids, are designed to detect changes in stretch and transmural pressure. Such changes are registered by afferent impulses that are transmitted by the carotid sinus nerves to nuclei in the brain stem. In response, efferent impulses are carried through sympathetic and vagus nerves to the heart and blood vessels, controlling heart rate and vasomotor tone. Carotid massage is used by physicians to diagnose Carotid Sinus Hypersensitivity ("CSH"), a condition in which mechanical deformation of the carotid sinus causes exaggerated bradycardia or vasodilatation responses, resulting in hypotension, presyncope, or syncope. Carotid massage also used as a bedside technique by physicians for non-pharmacologic rapid treatment of tachy-arrhythmias such as paroxysmal atrial tachycardia (PAT). In one embodiment of the invention, the carotid clip is used to provide controlled pressure on the carotid sinus in the diagnosis and management of CSH.

Figure 4:
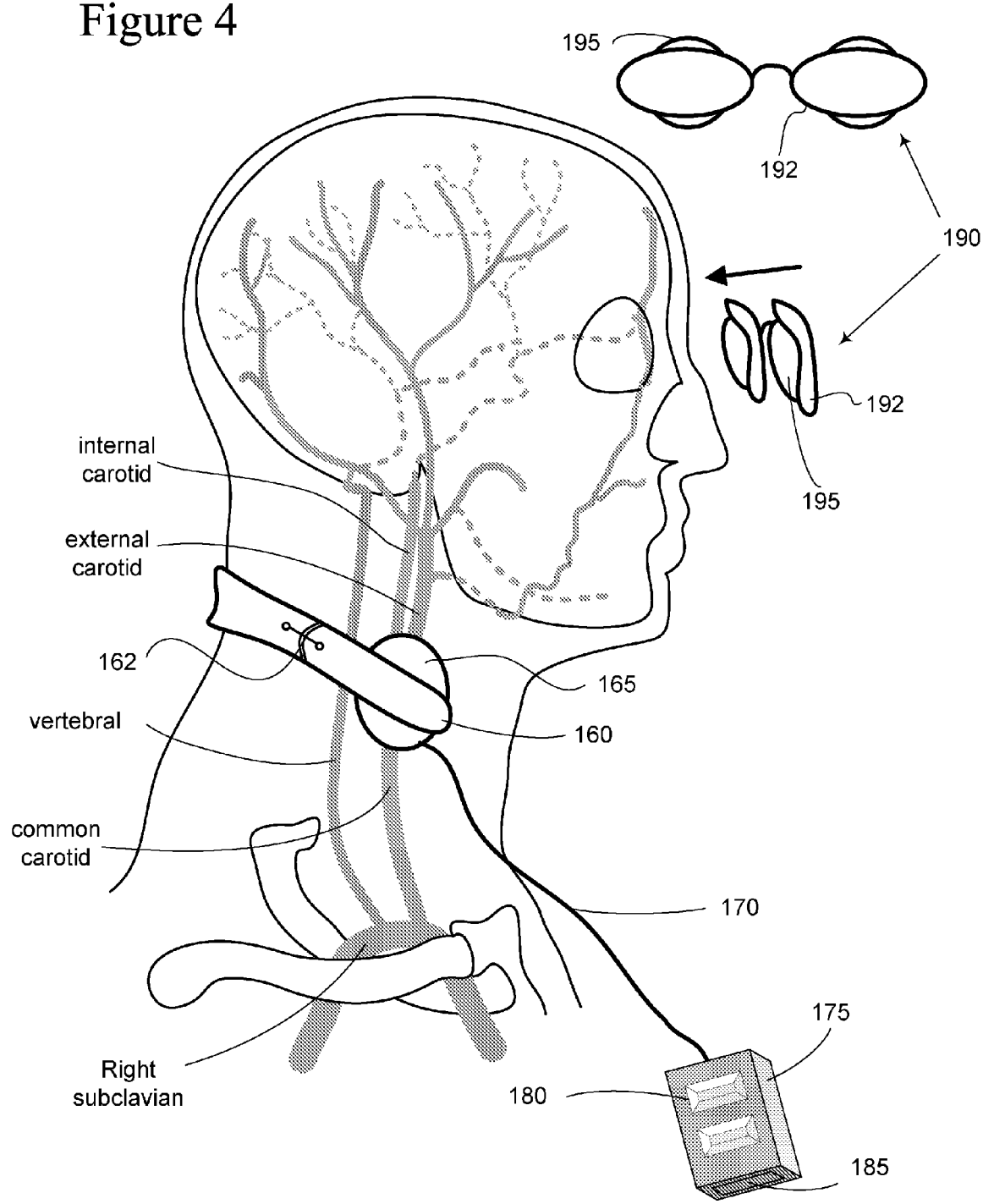
FIG. 4 depicts appliances for carotid and ocular message.

One embodiment of the invention, the carotid sinus reflex is exploited in order to provide a method for modulating the ANS to favor the parasympathetic and thereby induce smooth muscle relaxation in the treatment of a number of disorders including urinary retention. For one example as depicted in FIG. 4, a neck clip or band 160 is provided that includes a pad 165 that is dimensioned to create external pressure, and optionally massage and/or heat, on the carotid sinus. The clip can optionally provide for adjustment via a slide mechanism 162 such that the clip or band can be fitted to accommodate the dimensions of the patient's neck size and the individual location of the carotid bifurcation. For delivery of heat and vibration, the pad 165 is connected via a lead 170 to a controller 175 that includes on-off switches such as toggle switches 180. For devices including heating and vibration capability, the controller may include a battery 185 or may alternatively provide for connection to an external source of power such as an AC source. Prior to dispensing the device, the patient is tested using the device to insure that the patient is free of CSH, for which the device would be contraindicated.

The patient is educated to place the stimulator at the location of the maximal carotid impulse, medial to the sternomastoid muscle at the upper border level of the thyroid cartilage. Pressure, heat and vibration can be gauged and controlled by such a device. The purpose of the device is to standardize the technique of placing increased pressure at the carotid sinus to shift the ANS balance towards the parasympathetic but without inducing asystole or a dangerous reduction of blood pressure. However, by allowing the patient to control the placement, pressure, degree of heating and vibration, the required stimulation is provided. In one embodiment, the device is further provided with a blood pressure monitor and may include an alarm if blood pressure drops below a preset level.

Ocular Massage: In another embodiment, ocular massage is employed to increase parasympathetic tone. Ocular massage is a procedure that involves applying pressure (compression) on the eyes and, like carotid message, is employed to stop PAT. In one embodiment, an eyepiece such as eyepiece 190 depicted in FIG. 4 device is provided that includes a frame 192 dimensioned to fit over both eye sockets and to support eyepads 195 provide gentle pressure, with or without heating, as needed to stimulate a parasympathetic response and thereby enable urination or defecation. The eyepads 195 can be solid such as foam or can be filled with a variety of materials known in the art. In one embodiment, the eyepads are filled with a fluid or gel that can be heated for use such as in a microwave. The device can be conveniently carried in a purse or pocket until needed.

Treatment of Heart Failure: In other embodiments, heat is used to treat heart failure where increased production of nitric oxide is needed. In this embodiment, long term usage is envisioned for providing generalized or systemic vasodilation by shifting the sympathetic-parasympathetic balance and increasing local production of nitric oxide. The applied heat is delivered below the individual's tolerance or comfort level and is applied slowly and increased in accordance with individual comfort such that the application of heat does not cause stress or exceed a person's tolerance, in which case a sympathetic surge and overtone may be provoked. In one embodiment for the treatment of heart failure, a heating garment can be employed as often as desired, for example, several times a day on a manual or timed schedule.

The invention provides heating garments including underwear, vests and body suits, and wearable heating accessories like gloves and socks for heart failure patients who are in a vasoconstrictive mode, which is a well known stage of heart failure. Vasoconstriction caused by excess sympathetic activity in turn causes a failing heart to pump harder against a higher vascular resistance. As evidence of this, heart failure patients typically have cold fingers (extremities). Specialized heating devices are provided that can enable partial or total body heating on a controlling degree of heating and timing cycle that avoid the stress of too much heat. In one embodiment, an astronaut type cloth garment is provided that allows the patient to control the heat at different spots with different temperatures. If desired, the amount of heat can be titrated by monitoring blood pressure or by brain natriutic peptide levels (BNP) a well known serum marker of response to therapy. The heat is controllable to be administered slowly and should not increase heart rate beyond a level where it crosses individual's tolerance and increases significantly the activity of cardiovascular system. In one embodiment, a pulse monitor is included with the device such that the heating cycle is turned off or down when a predetermined decrease in heart rate is reached.

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

I claim:

1. A method for control of bladder function, comprising:
   a) preparing the bladder for voiding comprising placing a non-invasive controlled heating device on skin areas with neuromodulatory links to the bladder; and
   b) turning on the non-invasive controlled heating device prior to voiding.

2. A method for control of bladder function, comprising:
   a) preparing the bladder for voiding comprising turning on a controlled heating device;
   b) applying heat to a skin areas with neuromodulatory links to the bladder prior to voiding; and
   c) using heating in conjunction with a pharmacologic approach to treatment of bladder voiding disorders such as hesitancy.

3. The method of claim 2, wherein the pharmacologic approach comprises treatment with a drug selected from the group consisting of: alpha blockers and muscarinic receptor agonists, and combinations thereof.

4. The method of claim 1, further comprising employing one or more non-pharmacologic techniques selected from the group consisting of: electric, magnetic, and/or electromagnetic neuromodulating devices used to modulate local neuronal activity in a target muscle system proximal to the bladder.

5. A method of control of bladder function, comprising:
   a) preparing the bladder for voiding comprising turning on a controlled heating device wherein the device is wearable;
   b) applying heat on skin areas with neuromodulatory links to the bladder.

6. A method for control of bladder function, comprising:
   a) preparing the bladder for voiding comprising turning on a controlled heating device wherein the device is worn in association with, or disposed in, underwear; and
   b) applying local heat to skin areas with neuromodulatory links to the bladder prior to voiding.

7. The method claim 1, wherein the heat is provided in treatment of one or more of urinary hesitancy, shy bladder and nocturia conditions.

8. A method for control of bladder function, comprising: turning on a non invasive heating element disposed in a wearable appliance that applies heat to a body area distal to the bladder when voiding of the bladder is desired; and turning off the heating element when voiding of the bladder is completed.

9. The method of claim 8, wherein the area is one or more of: face, fingers, and toes.

10. The method of claim 8, wherein the appliance is disposed in, or in association with, a garment selected from the group consisting of: gloves, socks, shoes, helmets, scarves, jackets, and vests.

11. A method for control of bladder function in an individual, comprising:
   turning on a heat source disposed in non-wearable fixed or portable appliance that delivers heat locally at the skin level that triggers a neuromodulatory effect on the bladder neck through the autonomic nervous system to the individual when voiding of the bladder is desired; and
   turning off the heat source when voiding of the bladder is completed.

12. The method of claim 11, wherein the appliance delivers radiant heat, warm air, or a warm hand hold.

13. The method claim 11, wherein the heat is provided in treatment of one or more of urinary hesitancy, shy bladder and nocturia conditions.

* * * * *